United States Patent

Wynn

[11] 4,193,692
[45] Mar. 18, 1980

[54] METHOD AND APPARATUS FOR THE OPTICAL MEASUREMENT OF THE CONCENTRATION OF A PARTICULATE IN A FLUID

[75] Inventor: William H. Wynn, Hillsborough, Calif.

[73] Assignee: Monitek, Inc., Redwood City, Calif.

[21] Appl. No.: 913,356

[22] Filed: Jun. 7, 1978

[51] Int. Cl.$^2$ ............................................ G01N 15/06
[52] U.S. Cl. ...................................... 356/341; 356/343
[58] Field of Search ............... 356/341, 343, 435, 402;
250/565, 575; 364/525, 555, 808, 841, 850

[56] References Cited

U.S. PATENT DOCUMENTS

| | | | |
|---|---|---|---|
| 3,420,609 | 1/1969 | Kozawa | 356/341 X |
| 3,518,437 | 6/1970 | Riggs | 356/341 X |
| 3,576,558 | 4/1971 | Devries | 356/341 X |
| 3,653,768 | 4/1972 | Menke | 356/341 |
| 3,988,591 | 10/1976 | Killer | 250/56 5 |

Primary Examiner—John K. Corbin
Assistant Examiner—Matthew W. Koren
Attorney, Agent, or Firm—Lowhurst & Aine

[57] ABSTRACT

An optical concentration measuring apparatus and method which provides an output signal which is a substantially linear function of the concentration. The apparatus includes a chamber for containing a fluid sample and a source of optical radiation which develops a beam which is transmitted through the chamber and the sample. A first photoelectric cell is disposed to receive the transmitted beam for generating an electrical signal commensurate with the intensity of the beam after passage through the chamber and the fluid sample, and a second photoelectric cell which is disposed at a selected angle with respect to the direct beam for providing an electrical signal commensurate with the light scattered in a direction corresponding to the selected signal. The signal commensurate with the scattered beam and the signal commensurate with the direct beam are applied to a signal processor which develops a ratio of these signals, one of the signals being multiplied by a constant. The method allows this constant to be selected so that a signal from the signal processor is substantially linear with the particulate concentration.

5 Claims, 7 Drawing Figures

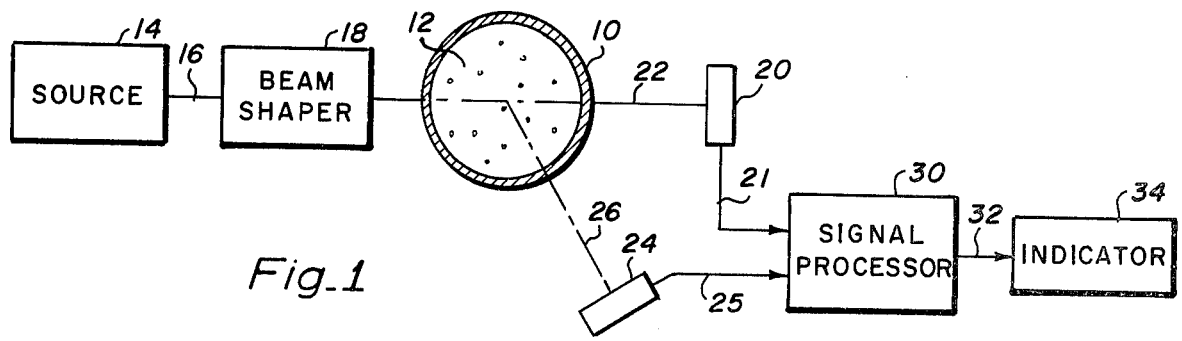
Fig_1
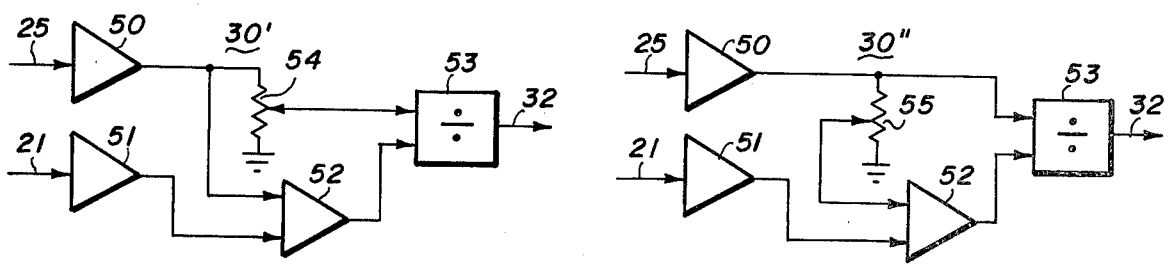
Fig_2A  Fig_2B
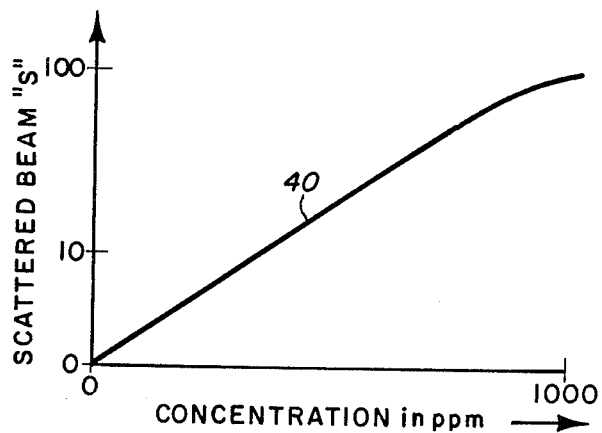
Fig_3A
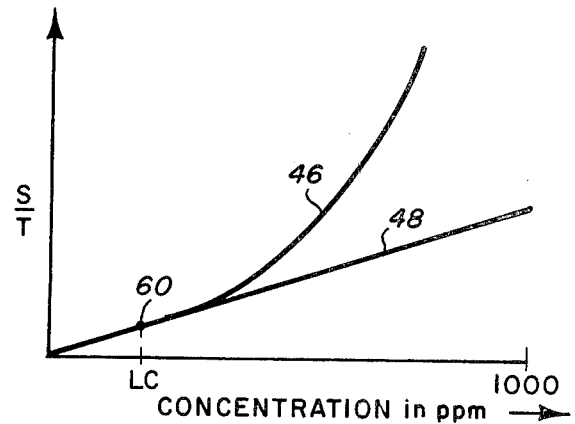
Fig_3C
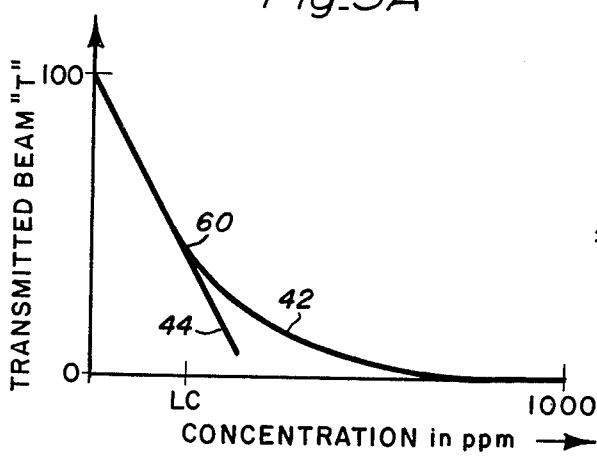
Fig_3B
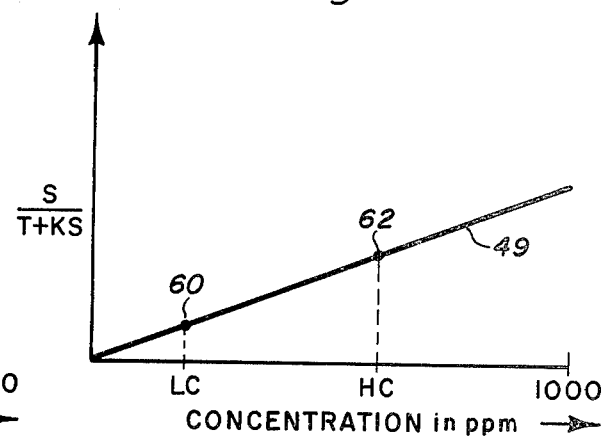
Fig_3D

METHOD AND APPARATUS FOR THE OPTICAL MEASUREMENT OF THE CONCENTRATION OF A PARTICULATE IN A FLUID

BACKGROUND OF THE INVENTION

This invention relates generally to apparatus for optically measuring the concentration of a particulate in a fluid and to a method of linearizing the relationship between the particulate concentration and the signal developed by the apparatus over at least two orders of magnitude of concentration values.

Among the prior art of interest are the U.S. Pat. Nos. 3,420,609 to Kozawa; 3,713,743 to Simms; 3,724,957 to Tamate et al; and 4,047,815 to Sedlacek.

Concentrations of a particulate in a fluid, generally speaking, refers to the nature and the amount of discrete aggregations of material in the fluid which differ from the pure fluid itself. In case of liquids, and when optical properties are most important, the term "turbidity" is often used and is observed as the degradation of the contrast of an image transmitted through the liquid (for example the Jackson candle technique) or as a percentage of light emerging from the sample at angles different from the direct transmitted beam.

One measurement of concentration, which is in common use in the prior art, is to pass a beam of optical radiation, such as light, through the fluid, measure the intensity of the transmitted light and of light scattered at a preselected angle, and develop the ratio of the scattered light to the transmitted light. More particularly, the prior art method is to plot the ratio for two known concentrations on a graph and utilize the slope of the line (rate of change) passing through the two points as a function of the concentration. As long as the concentration of the particulate in the fluid has values which are less than say 200 parts per million (ppm), the assumption that the concentration varies linearly with ratio of the scattered to the transmitted light presents a fairly good approximately to the actual behavior of the relationship. At values greater than 200 ppm, the relationship becomes nonlinear.

The reasons for the nonlinearity of the relationship of the ratio to the concentration at higher values of particular concentration are not entirely understood, but the following factors contribute to it. When the concentration is low, most of the light is transmitted and very little of the light is scattered so that the scattered light is small and the transmitted light is large and the ratio would therefore be small. When the concentration increases, the scattered light also increases and diminishes the transmitted light. Also, the particulate will absorb light which is neither scattered nor transmitted and which will therefore not follow Beers law which gives the intensity of the transmitted light as a function of concentration.

While it is, of course, possible to plot the relationship between the ratio of scattered to direct light for known concentrations, and use that graph to determine any unknown concentrations, it is often desirable to develop a measurement signal that is linear with concentration. Such a linear relationship makes it more convenient to apply to meters, counters, controllers and the like.

One method heretofore utilized to linearize the relationship between concentration and a measured quantity is to apply the ratio signal (scattered over direct) to a linearizing network and utilize the output of such a linearizing network. However, such networks are expensive to design and to manufacture, and require individual adjustment for each measuring apparatus.

SUMMARY OF THE INVENTION

It is therefore a primary object of the present invention to process the signals commensurate with the scattered beam and the direct beam in such a manner that the processed signal becomes a substantially linear function of the concentration.

It is another object of the present invention to provide an apparatus for the optical measurement of particulate concentration that develops an output signal which is a linear function of the concentration.

It is still a further object of the invention to provide an improved concentration measuring apparatus and method, utilizing a direct and a scattered beam of optical radiation and a processing means, which processes the signal commensurate with the scattered and the direct beams in such a manner that the concentration and the processed signal are related to one another substantially linearly.

In accordance with a preferred embodiment of the present invention, the signal processing means derives a processed signal which is equal to the ratio of the signal commensurate with the scattered beam and the sum of the signal commensurate with the direct beam and the signal commensurate with the scattered light, the latter being multiplied by a preselected constant. To determine the magnitude of the constant, a first measurement of the ratio of the scattered beam and the direct beam is made using a known concentration of less than two hundred parts per million and plotted on a graph. Then a line is drawn through that point and a point corresponding to zero concentration, this line representing the rate of change of concentration with the scattered over direct beam ratio. Thereafter, a second measurement of a concentration in excess of 200 ppm is performed and the ratio provided by the signal processor is developed. Then the constant is adjusted so that the processed signal has a value which falls on the previously plotted line.

BRIEF DESCRIPTION OF THE DRAWINGS

FIG. 1 is a schematic drawing, partially mechanical and partially electrical, of the concentration measuring apparatus of the present invention;

FIGS. 2A and 2B are schematic electrical diagrams of the signal processor shown in FIG. 1; and FIGS. 3A, 3B, 3C and 3D are graphs respectively showing the variation of four electrical signals with concentration, namely the scattered beam, transmitted beam, ratio of the scattered to the transmitted beam, and the signal developed by the signal processor.

DETAILED DESCRIPTION OF THE EMBODIMENT

Referring now to FIG. 1 of the drawings, there is shown the concentration measuring apparatus of the present invention including a chamber 10 for containing a fluid sample 12 to be evaluated, a source of optical radiation 14 which provides an optical beam 16 which is shaped by a beam shaper 18 to form a substantially parallel beam. The term optical radiation, as used herein, refers to electromagnetic radiation extending from the long end of the infrared region to the short end of the ultraviolet region and therefore including the entire visible spectrum.

There is also provided a first optical radiation detector 20 which is located on the optical axis 22 of source 14, and a second optical radiation detector 24 which is located on a scatter axis 26 which makes a preselected angle with optical axis 22. The walls of chamber 10 are transparent to the optical radiation employed. Chamber 10 may be in the form of a tube connected into a process stream for metering or monitoring the concentration of particulate in the fluid stream, or may be a closed vessel for investigating the properties of a particular stationary sample of the liquid.

Detectors 20 and 24 may be photoelectric cells in case that the optical radiation is in the visible spectrum or other suitable devices in case the radiation is in the infrared or the ultraviolet region. Each detector provides an output signal which is commensurate with the radiation received by it. Detector 20 is placed on the optical axis to measure the amount of optical radiation transmitted through the liquid which is usually referred to as the transmitted beam or the direct beam, and detector 24 is placed on the selected scattering axis 26 to measure the amount of optical radiation scattered by the particulate in fluid 12 which is usually referred to as the scattered beam. The direct beam signal "D" from detector 20 and the scattered beam signal "S" from detector 24 are applied to a signal processor 30 that develops a processed signal on line 32 which is applied to an indicator 34 which gives an indication of the amplitude of processed signal 32. Indicator 24 may be a voltmeter either of analog or digital form or may be a graphic plotter in case liquid 12 is a flowing stream that is being monitored or measured.

Referring now to FIG. 3, there are shown four graphs which respectively illustrate the variations of the signals developed by detectors 20 and 24, as well as certain functions of these signals, as a function of the concentration in parts per million (ppm). More particularly, FIG. 3A shows a curve 40 which represents the signal developed by detector 24 as a function of concentration. This curve shows that for low ranges of concentration, the electrical signal commensurate with the scattered beam is substantially linear which is readily explained, because for small concentrations the amount scattered is directly related to the number of particles in the fluid and the greater the number of particles, the more light is scattered. However, as the concentration approaches about 800 ppm, other factors will enter such as absorption and also interference with scattering in that light scattered from one particle may be blocked or rescattered by other particles, a phenomena that increases with increasing concentration, so that the scattered signal peaks and then slowly decreases. The significant point is that, for low concentration, the relationship between the strength of the scattered beam is subsequently linear with concentration until the concentration exceeds about 800 ppm.

Referring now to FIG. 3B, there is shown a curve 42 representing the output signal of direct beam detector 20 as a function of concentration. This curve follows a relationship known as Beers Law which holds that the direct signal is a function of the logarithm of the reciprocal of the amount of light transmitted. It is again seen that for low concentrations, say below about 200 ppm, the relationship between the direct beam signal and the concentration is linear, see line 44, and thereafter the signal decreases less rapidly and approaches zero asymptotically.

Curve 42 is also readily explainable in that the amount of light transmitted for very low concentration is substantially the entire beam and, as the concentration increases, loses a certain amount due to scattering. In addition to losing energy by scattering, the direct beam also loses by absorption and its linear region is much smaller than the linear region of the scattered beam illustrated in curve 40.

Referring now to FIG. 3C, there is shown a curve 46 which depicts the relationship of the ratio "P" of the scattered beam S to the direct beam D as a function of concentration. It will be seen that this curve is substantially linear in the region in which curve 42 is linear, say up to about 100 or 200 ppm and then becomes fairly nonlinear. The linear region gives the slope of line 48 which represents the true rate of change of signal "P" with concentration for low concentrations. One way of measuring the concentration of a particulate contained in fluid is to plot curve 46 for known values of concentration and then using this graph to find the unknown concentration after the signal corresponding to the scattered to direct beam is obtained.

In accordance with the present invention, it has been found that the ratio of the scattered beam to the sum of the direct beam plus the scattered beam multiplied by a constant K is substantially a linear function of the concentration over a range of several orders of magnitude. Mathematically expressed, this ratio "R" is $$R = S/D + KS$$

wherein K is a constant that is experimentally adjusted so that R, for high concentrations, say above 200 ppm becomes, falls on curve 48 of FIG. 3C. Once K is adjusted, as will be explained hereinafter in more detail, R will be useful to meaure the concentration over a range of several orders of magnitude.

Referring now to FIG. 3D, there is shown curve 49 which depicts the relationship between signal R and the concentration. As can be seen, curve 49 is linear and has a slope that is equal to that of curve 48, the slope being adjusted constant K.

Referring now to FIGS. 2A and 2B of the drawing, in which like reference characters designate like parts, there are shown a pair of amplifiers 50 and 51 to which the signals from detector 24 and 20 are applied respectively, the signal from detector 24 being applied to amplifier 50 and the signal from detector 20 being applied to amplifier 51. There is also provided a summing amplifier 52, and the output of amplifier 52, as well as the output of amplifier 50 are applied to a conventional divider 53 which develops, at its output terminal, processed signal R on line 32.

Referring now specifically to FIG. 2A, the output of amplifier 50 is applied to the input of summing amplifier 52 and to one side of an adjustable potentiometer 54, the other side being grounded. The adjustable tab is coupled to divider 52, and adjustment of potentiometer 54 changes the signal strength of the signal applied to the divider, this being KS.

Referring now to FIG. 2B, the output of amplifier 50 is applied directly to divider 53, as well as to one side of potentiometer 55 the other side of which is grounded. The adjustable tab is coupled to the input of summing amplifier 52. Adjustment of potentiometer 55 changes of the signal strength of the signal applied to summing amplifier 52.

Both signal processors 30' and 30'' develop the ratio of the scattered beam to the direct plus the scattered beam, the latter being multiplied by a constant. The signal processor of FIG. 2A has potentiometer 54 placed such that it allows for K being smaller than one and the signal processor of FIG. 2B has the potentiometer 55 placed such that it allows for K being greater than one.

In practicing the present invention, the first step is to use the apparatus of FIG. 1 with liquid sample 12 having a low, known, concentration "L.C." which is less than 200 ppm, preferably not higher than 50 ppm, to take advantage of the linear region of the transmitted beam as shown in curve 42 of FIG. 3B and indicated by line 44. The point on the curve corresponding to L.C. ppm represents the concentration at the end of the linear region which is marked by reference character 60 and is typically 50 ppm.

In other words, the optimum concentration for taking point 60 would be to use the highest concentration which is still in the linear region of curve 42 and which has been found to be approximately 50 parts per million. After having selected a low concentration, the ratio of the scattered beam "S" to the direct beam "D" is developed and point 60 is plotted on the graph shown in FIG. 3D. Point 60 is then connected to the zero point to form line 49 which represents the rate of change of the ratio of the scattered beam S to the transmitted beam D with concentration which is linear as shown in FIG. 3C because both the scattered beam and the transmitted beam are in the linear region as seen by line 48.

Thereafter, a known, high concentration "H.C." is selected which should be at least twice as great as the low concentration selected to establish the slope of line 49, and preferably, H.C. should be in the region of greatest interest such as 1000 ppm. After selecting a known, high concentration, the signals S and D are applied to signal processor 30 which develops the processed signal R which includes the constant K. Thereafter, the constant K is adjusted by means of potentiometers 54 or 55 until R has a value which coincides with point 62 on curve 49, this point being the value of signal R at known concentration H.C. for a rate of change of signal with concentrations which correspond to the rate of change previously established for the low concentration.

There has been described a means and a method of linearizing the relationship between the concentration of a particulate containing fluid and an electrical signal, developed from the direct beam detector and the scattered beam detector, that is linear over several orders of magnitude, say from a very low concentration to perhaps 10,000 ppm. This linearization is achieved without the necessity of having to provide a special linearizing network following a processor developing the simple ratio of the scattered to the transmitted beam P, but instead employs a slightly more complex signal processor which linearizes the relationship by adding to the direct beam signal in the denominator the scattered beam component suitable multiplied by a selectable constant K.

What is claimed is:

1. The method of measuring the concentration of a particulate in a fluid by optical means utilizing a beam of optical radiation, comprising the steps of:
   deriving a first electrical signal "D" commensurate with the optical radiation transmitted through the particulate containing fluid;
   deriving a second electrical signal "S" commensurate with the optical radiation scattered by the particulate containing fluid;
   deriving a third electrical signal "R" which is equal to the ratio of $S/[D+KS]$, where K is a constant; and
   selecting the constant K such that the relationship between C and R is substantially linear, where C is commensurate with the concentration of the particulate contained within the fluid.

2. The method in accordance with claim 1 in which the scale factor K is selected by first deriving a fourth electrical signal "P" which is commensurate with the ratio of said second electrical signal "S" to said first electrical signal "D" for a low, known, particulate concentration of less than 200 parts per million to establish a rate of change line of concentration versus "P" for low concentrations of particulate; and thereafter deriving said third electrical signal R for a high, known, particulate concentration which is at least twice as high as said low concentration, and adjusting said constant K so that the amplitude of said third signals R falls on said rate of change line.

3. The method of measuring concentration of a particulate in a fluid by optical means, utilizing a beam of optical radiation, comprising the steps of:
   deriving a first electrical signal "D" commensurate with the optical radition transmitted through the particulate containing fluid;
   deriving a second electrical signal "S" commensurate with the optical radiation scattered through the particulate containing fluid;
   deriving a low concentration electrical signal "P" commensurate with the ratio of S/D when the particulate concentration is known and is less than about 200 parts per million, and utilizing said low concentration signal to determine a linear rate of change of signal P with particulate concentration;
   deriving a high concentration electrical signal "R" commensurate with the ratio of $S/[KS+D]$ when the particulate concentration is known and is at least twice as high as said low known concentration, and selecting the constant "K" such that said high known concentration has the same value as would have been obtained by using said low concentration rate of change; and
   utilizing said high concentration electrical signal "R", with the selected value for concentrate "K", to determine the value of any unknown high and low concentration.

4. A concentration measuring apparatus comprising:
   an optical radiation transparent chamber for containing a fluid sample to be evaluated;
   a source of optical radiation disposed on one side of said chamber and including means for forming a beam and for directing the beam from said source through said chamber and said fluid sample within said chamber to define a transmitted beam;
   first photoelectrical means on the other side of said chamber and disposed to receive said transmitted beam, said first means generating a first signal commensurate with the intensity of the beam after transmittion through said chamber and said sample;
   second photoelectric means disposed for receiving radiation scattered by said sample in a selected direction, said second photoelectric means developing a second signal commensurate with the intensity of the scattered radiation in said selected direction; and signal processing means responsive to said first and said second signal operative to provide a processed signal which is commensurate with the ratio of said second signal to the sum of said first signal and a third signal, said third signal being equal to said second signal multiplied by a preselected constant, said output signal being linearly related to the concentration of the particulate in said fluid sample.

5. In a concentration measuring apparatus which includes, an optically radiation transparent chamber which contains a fluid sample to be evaluated, a source of optical radiation disposed for transmission through said chamber, and a pair of radiation sensing devices, one being placed to develop a signal commensurate with the transmitted radiation and another positioned to develop a signal commensurate with the radiation scattered in a selected direction, and signal processing means responsive to the said signals, the improvement in the signal processor comprising:

signal processor means responsive to the signal commensurate with the transmitted radiation and the scattered radiation and operative to develop a processed signal which is commensurate with the ratio of the scattered radiation signal to the sum of the transmitted signal plus the scattered radiation signal, the scattered radiation signal being multiplied by a constant whose value is selected to linearize the processed signal with concentration.

* * * * *